(12) United States Patent
Cordaro et al.

(10) Patent No.: US 11,547,457 B2
(45) Date of Patent: Jan. 10, 2023

(54) ANTERIOR CERVICAL PLATE WITH INTEGRATED LOCKS

(71) Applicants: Nicholas Cordaro, Encinitas, CA (US); Andres Talamantes, Vista, CA (US); Michael DiLauro, Carlsbad, CA (US)

(72) Inventors: Nicholas Cordaro, Encinitas, CA (US); Andres Talamantes, Vista, CA (US); Michael DiLauro, Carlsbad, CA (US)

( * ) Notice: Subject to any disclaimer, the term of this patent is extended or adjusted under 35 U.S.C. 154(b) by 29 days.

(21) Appl. No.: 17/025,256

(22) Filed: Sep. 18, 2020

(65) Prior Publication Data

US 2021/0077165 A1 Mar. 18, 2021

Related U.S. Application Data

(60) Provisional application No. 62/901,835, filed on Sep. 18, 2019.

(51) Int. Cl.
*A61B 17/80* (2006.01)
*A61B 17/70* (2006.01)

(52) U.S. Cl.
CPC ...... *A61B 17/8042* (2013.01); *A61B 17/7059* (2013.01)

(58) Field of Classification Search
CPC . A61B 17/7059; A61B 17/80; A61B 17/8033; A61B 17/8042; A61B 17/8052; A61B 17/8057
See application file for complete search history.

(56) References Cited

U.S. PATENT DOCUMENTS

| 6,193,721 B1 * | 2/2001 | Michelson | A61B 17/1604 606/76 |
| 2017/0202585 A1 * | 7/2017 | Leak | A61B 17/8052 |
| 2018/0103989 A1 * | 4/2018 | Altarac | A61B 17/7059 |
| 2019/0038318 A1 * | 2/2019 | Tempco | A61B 17/863 |
| 2021/0030545 A1 * | 2/2021 | Walsh | B33Y 80/00 |

* cited by examiner

*Primary Examiner* — Si Ming Ku
(74) *Attorney, Agent, or Firm* — Brennan, Manna & Diamond, LLC

(57) ABSTRACT

An anterior cervical plate system with integrated locks which is additively manufactured as one component is disclosed. The anterior cervical plate system comprises a plate having at least one through hole configured to receive a bone screw for attaching the plate to a patient's bone. The plate includes a lock component adjacent to the at least one through hole. The lock component is connected to the plate such that the lock component is permitted to rotate with respect to the plate. The lock component has an unlocked position in which the locking ends of the lock component do not cover the head of the bone screw inside the through hole, and a locked position in which at least part of the locking ends engage the head portion of the bone screw to prevent the bone screw from backing out of the through hole.

17 Claims, 3 Drawing Sheets

ANTERIOR CERVICAL PLATE WITH INTEGRATED LOCKS

CROSS-REFERENCE TO RELATED APPLICATION

The present application claims priority to, and the benefit of, U.S. Provisional Application No. 62/901,835, which was filed on Sep. 18, 2019 and is incorporated herein by reference in its entirety.

FIELD OF THE INVENTION

The present invention relates generally to an anterior cervical plate having integrated locks. More specifically, the anterior cervical plate with integrated locks is additively manufactured as one unitary component.

BACKGROUND OF THE INVENTION

Anterior cervical plates are used for a variety of conditions to immobilize, stabilize, or align cervical vertebrae. For example, after cervical spinal fusion surgery, cervical plates are used to add strength and rigidity to the adjoined vertebrae, increase the rate of fusion between plates and can help reduce the need for external bracing after surgery. Also, cervical plates secure vertebrae together where an intervening vertebra has been removed or replaced. In other cases, cervical plates are used to correct instability in the cervical spine caused by trauma, tumors, advanced degenerative discs, infection or congenital or acquired deformities.

A typical cervical plate includes an elongated rectangular plate that spans the distance between two or more vertebrae. The plate is curved to match the natural curvature of the spine at the location to which it is attached and bone screws or pins are used to fasten the plate to the vertebral bodies. A pair of apertures is formed at one end of the plate for passing bone screws through and into a first vertebral body to secure the first end of the plate to the first vertebral body. A second pair of apertures is formed at the other end of the plate for passing bone screws through and into a second vertebral body to secure the second end of the plate to the second vertebral body. Through this arrangement, the plate bridges two vertebral bodies. More vertebrae may be connected with a longer plate and a corresponding increased number of bone screw apertures and the corresponding bone screws or pins inserted through the apertures at the intervening vertebral levels.

The cervical spine can be surgically approached anteriorly or posteriorly. In an anterior cervical fusion surgery, an incision is made and the spine is approached from the front of the patient. The carotid sheath, muscles, trachea and esophagus are moved laterally to expose and provide access to the cervical spine. Holes are drilled into the vertebral bodies or self-tapping screws are employed. The cervical plate is properly aligned on the vertebrae for the receipt of mounting screws and the plate is carefully and firmly attached to the cervical spine. With the plate in position, the vertebrae are held by the plate in desired spatial relationships and orientations relative to each other, pressure is removed from the nerve roots and pain caused by the herniated disc or other condition is relieved.

Over time, the interface between the screws and the bone and hence the plate itself, may present some problems of stability. Due to the anatomical structure of the cervical spine and the extreme anatomical forces that are brought to bear on the skeleton and transmitted to the cervical spine, the screws or other fasteners such as rods, securing the plate to the spine may loosen due to vibrations or toggle out of position. Also, the degeneration of vertebral bone quality may result in the screws loosening or becoming dislodged. As a result, bone screws securing the plate to the spine may move or back out of the vertebral body and plate disrupting the orientation and positioning of the vertebrae. Due to the relative location to the esophagus and other connective tissue, if the bone screws or other fasteners such as rods, securing the plate to the cervical spine backs out or loosens, the bone screw could impinge on or contact the adjacent tissue causing damage and increasing the pain suffered by the individual. Also, loosened screws may result in instability of the joint and lead to increased pain from the original injury or surgery for the patient.

Therefore, there is a need to provide a new and improved anterior cervical plate that resists bone screws or other fasteners such as rods, from backing out of the plate and also from being loosened with respect to the plate before migrating out of the aperture in which the screws were originally positioned. The anterior cervical plate must have a low profile due to the proximity of the implant site to the esophagus, nerves and other sensitive surrounding tissue. Furthermore, there is a need for the anterior cervical plate to withstand anatomical forces and for the plate to be easily implanted. Also, the locking mechanism must be easily activated by the surgeon or other personnel in the surgical theatre. This invention, as described in the detailed description, sets forth an improved anterior cervical plate with integrated locks to provide anti-back out protection for the bone screws or other fasteners such as rods, used to hold the cervical plate in position and prevent damage to the surrounding tissue and pain to the patient.

While this specification makes specific reference to an anterior cervical plate, it will be appreciated by those of ordinary skill in the art that aspects of the present invention are also equally useable with other like applications and other such medical devices and/or addressing similar issues.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises an anterior cervical plate system with integrated locks which may be additively manufactured as one or a single component. The anterior cervical plate system comprises a plate having at least one through hole configured to receive a bone screw or other fastener for attaching the plate to a bone. The plate has an upper surface and a lower surface which is interconnected by side surfaces. The plate includes at least one lock component adjacent to the at least one through hole. The lock component is connected to the plate such that the lock component is permitted to rotate in a generally planar fashion with respect to the surface of the plate. A bone screw or other fastener is configured for insertion into the through hole such that the bone screw extends from the top surface of the plate, through the hole and into the bone beneath the plate. The lock component has an unlocked position in which the locking ends of the lock component do not cover the head of the bone screw inside the through hole permitting passage of the bone screw in or out of the through hole and a locked position in which at least part of the locking ends engage and cover the head portion of the bone screw to prevent the bone screw from backing out of the through hole.

In another embodiment of the present invention, the lower surface of the plate of the anterior cervical plate system is additively manufactured with a rough or textured surface creating a topography for boney on-growth. Thus, all surfaces of the anterior cervical plate are relatively smooth, except for the bone facing surface which has the enhanced surface. The bone facing surface would have a textured contoured field, profile or area to promote boney on-growth to the plate.

In a yet further embodiment of the present invention, a cervical spine plate system is presented and includes a plate having a top surface and a lower surface. The plate having a plurality of through holes and at least one visualization pathway, with the visualization pathway being an opening larger than one of the plurality of through holes. Each of the plurality of through holes is sized and configured to receive a fastener and each of the plurality of through holes permitting an angulation of the fastener from 0° to 15°. The lower surface of the plate having a pattern creating a topography covering at least a portion of the lower surface, wherein the pattern promotes bone growth, and at least one locking component having a locking end and a body portion. The at least one locking component is repositionable in both a horizontal plane and a vertical plane.

In a still further embodiment of the present invention, a surgical plate system for use in cervical procedures is described and comprises a plate having a top surface and a lower surface, with the lower surface having a topography other than smooth and covering at least a portion of the lower surface. The plate further comprises a plurality of through holes designed to receive bone screws, and a plurality of visual pathways extending through the plate from the top surface to the lower surface. A plurality of locking components are also provided, with at least one locking component adjacent at least one of the plurality of through holes, and each of the locking components are equally spaced apart from one another. Each of the locking components is comprised of a locking end and a body portion, and each of the locking components is movable in a horizontal plane to a locking position from an unlocking position to cover a head of a bone screw positioned within a through hole.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION OF THE INVENTION

Figure 1:
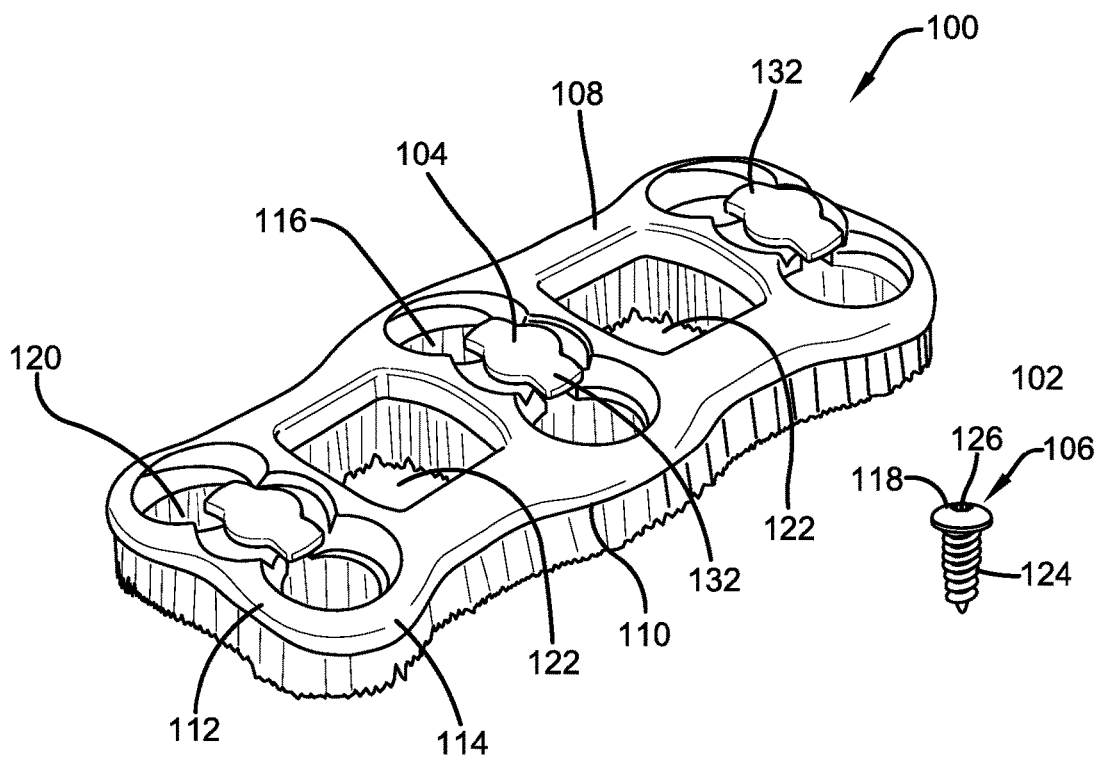
FIG. 1 illustrates a perspective view of one potential embodiment of the anterior cervical plate system having integrated locks of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Generally stated, and in one embodiment thereof, the present invention discloses an anterior cervical plate system having integrated locks which may be additively manufactured as a single unitary component. The anterior cervical plate system comprises a plate having at least one through hole or continuous opening therein configured to receive a bone screw or other fastener for attaching the plate to bone. The plate includes a moveable lock component disposed adjacent to the at least one through hole. The lock component is connected to the plate such that the lock component is permitted to rotate planarly with respect to the orientation of the plate. A bone screw is configured for insertion into the through hole so that it contacts the bone. The lock component is repositionable between an unlocked position in which the locking ends of the lock component do not cover or otherwise block the head of the bone screw inside the through hole, and a locked position in which at least a portion of the locking ends engage the head portion of the bone screw or fastener to prevent the bone screw or fastener from backing out of the through hole and releasing from the bone.

In another embodiment of the present invention, the lower surface of the plate of the anterior cervical plate system is additively manufactured with a roughened, contoured or textured surface to facilitate boney on-growth to the plate. The remaining surfaces of the anterior cervical plate are relatively smooth, except for the bone facing surface having the unique profile. The bone facing surface would have a textured topography to promote and aid boney on-growth to the plate.

Figure 2A:
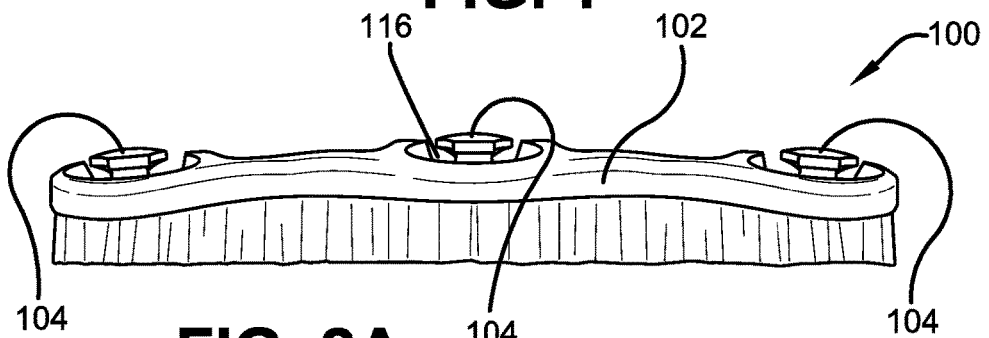
FIG. 2A illustrates a side perspective view of one potential embodiment of the anterior cervical plate system having integrated locks of the present invention in accordance with the disclosed architecture.
Figure 2B:
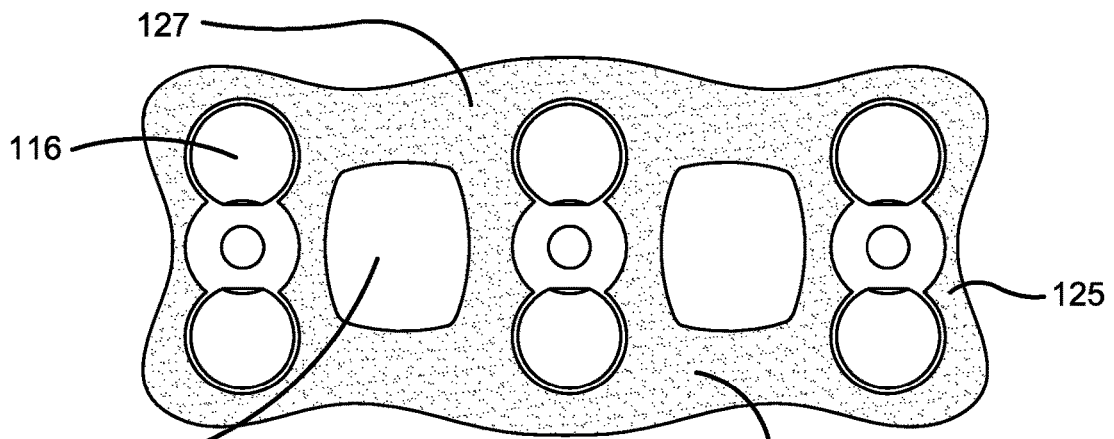
FIG. 2B illustrates a back perspective view of one potential embodiment of the anterior cervical plate system having integrated locks of the present invention in accordance with the disclosed architecture.
Figure 3A:
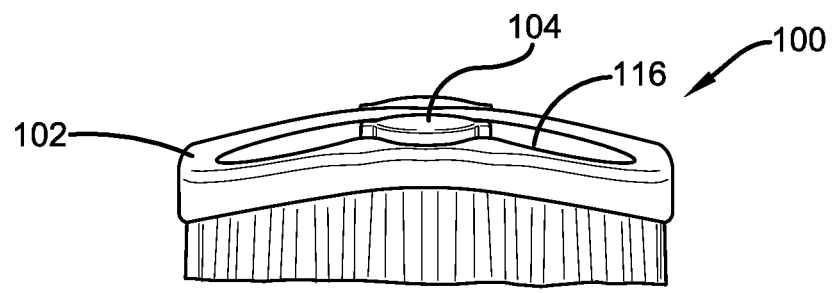
FIG. 3A illustrates a front perspective view of one potential embodiment of the anterior cervical plate system having integrated locks of the present invention in accordance with the disclosed architecture.
Figure 3B:
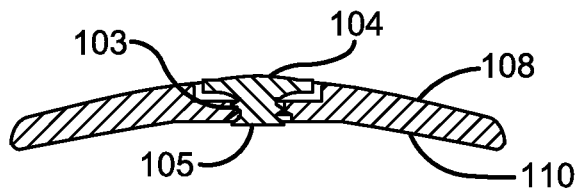
FIG. 3B illustrates a perspective view of one potential embodiment of a locking component of the anterior cervical plate system having integrated locks of the present invention in accordance with the disclosed architecture.

Referring initially to the drawings, FIGS. 1-3 illustrate generally an anterior cervical plate system 100 having integrated lock components 104. The plate system 100 may be used to stabilize or fuse vertebral bodies in the cervical or other region of the spine. The anterior cervical plate system 100 that is shown in FIGS. 1-3 is a two-level bone fixation plate that is configured to span across and fixate three vertebrae of the cervical spine. However, it should be understood that the invention is not so limited and the anterior cervical plate system 100 may be a single level or any multilevel anterior cervical plate spanning two or more vertebral bodies and/or may be used to span any two or more bone pieces of the human anatomy.

The anterior cervical plate system 100 comprises a plate 102 and lock components 104 for securing bone screws 106 or other fasteners such as rods to a bone. The plate 102 includes an upper or anterior surface 108 that faces the patient's soft tissue and esophagus when installed, and a lower surface or posterior surface 110 facing the vertebral bodies to be immobilized. The upper surface 108 and lower surface 110 are interconnected by curved side walls or end walls 112 to form a generally rectangular shape that is symmetrical about a longitudinal axis of the plate 102. The gently curved structure of the rectangular plate 102 complements the natural curved structure of the vertebral bodies and lordotic curvature of the cervical spine. The corners 114 of the plate 102 are typically rounded to reduce or eliminate irritation of the esophagus and the surrounding tissue that may be caused by sharp edges or corners. The plate 102 is positioned on top of the vertebral bodies and has a relatively low profile so as to minimally impinge on adjacent tissues. The plate 102 is sized and shaped for use on an anterior aspect of the cervical spine, although one skilled in the art may use the device in other regions of the spine as well. Generally speaking, the size of the plate 102 may range from 12 to 105 mm, wherein the size is selected based on the number of vertebrae or bone to be fused or treated during the procedure. For example, 20 mm to 34 mm and 37 mm to 55 mm are common lengths used in connection with cervical spine procedures. The thickness of the plate 102 should preferably not be significantly larger than the vertebrae to which it is being fused to, and as such the thickness may range for example from 0.5 mm to about 10 mm.

The plate 102 may be manufactured from stainless steel, cobalt, titanium and other suitable surgical metals, alloys or the like and in some applications, ceramic materials, carbon fiber and related composites may also be applicable. Other plates may be made from materials that dissolve over time, and after fusion with the bone occurs. The design of the plate 102 may aid in the compression to help in the bone fusion.

Additionally, the plate 102 and its components can be any suitable size, shape, and configuration as is known in the art without affecting the overall concept of the invention. One of ordinary skill in the art will appreciate that the shape and size of the plate 102 as shown in FIGS. 1-3 is for illustrative purposes only and many other shapes and sizes of the plate 102 are well within the scope of the present disclosure. Although dimensions of the plate 102 (i.e., length, width, and height) are important design parameters for good performance, the plate 102 may be any shape, size or configuration that ensures optimal performance during use.

The plate 102 and lock components 104 of the anterior cervical plate system 100 are typically manufactured using additive manufacturing (AM) techniques and grown as one or a single part to improve structural rigidity. Further, the posterior surface 110 of the plate 102 may be additionally configured to have a rough, textured or fuzzy topography or profile to promote boney on-growth to the plate 102. This trabecular surface would be produced during the additive manufacturing process as well and may take any number of configurations from a regular pattern to irregular, to shaped patterns appearing at regular or random areas of the plate. There may also be spaces between the topography such that spaces do not interfere with other areas where bone growth is to be promoted. Furthermore, the lock component 104 is preferably built with a positive inclination angle, such as 30 degrees or less, such that there would not be a flat surface under the head or main body of the lock component 104, which would produce angled features for the negative facing surfaces, which would give better feature quality.

FIG. 2A illustrates a side perspective view of one potential embodiment of the anterior cervical plate system having integrated locks of the present invention in accordance with the disclosed architecture, and FIG. 2B illustrates a back perspective view of one potential embodiment of the anterior cervical plate system having integrated locks. More specifically, FIG. 2B illustrates the back side of the plate 102, with through holes 116 and spaces 122. The pattern 123 of the topography is also graphically represented and showing areas with patterns created, and other areas 127 where there is no pattern such as in those areas adjacent to the spaces 122. FIG. 2B also illustrates shapes 125, which may be placed in a pattern or in a random arrangement.

Still referencing FIGS. 1-3, the plate 102 further comprises a plurality of through holes 116, as shown in the figures in this embodiment a total of 6 holes have been provided, extending through the cervical plate 102 from the upper surface 108 and through the lower surface 110. The holes 116 are configured to receive bone screws 106. Each hole 116 is slighted tapered to receive the bone screw 106 and to prevent the head portion 118 of the bone screw 106 from passing distally through the through hole 116. Further, the holes 116 are recessed from the upper surface 108 such that the head portion 118 of the bone screw 106 does not protrude beyond the upper surface 108 of the plate 102 in order to maintain a relatively low profile for the plate 102. Each through hole 116 has a larger exit opening 120 at the lower surface 110 to allow room for the angulation of inserted bone screws 106 so that the screws or rods can be angled into the bone to create a firmer fastening situation. The amount of angulation can depend on the particular procedure, and what is required to anchor the plate 102 to the patient's bone. The angulation can range from 0° to 15° and the angulation of the screw or rod positioned in each hole can be different from each of the other entry angles for the screws or rods to accommodate the required angle of entry. For example, the fasteners on one side or end of the plate 102 may be at 0°, and the fasteners on the other side of the plate can be at 5° or each fastener 106 may be variable as needed.

FIGS. 1-3 illustrate, in one embodiment, a plate 102 having three sets of through holes 116 spaced generally equally apart along the plate centerline for driving bone screws or other fasteners 106 into and stabilizing three vertebral bodies for creating a two-level construct. Each set of through holes 116 includes two holes 116 opposingly spaced from each other along the centerline of the anterior cervical plate 102. Each set of through holes 116 is adapted for receiving two bone screws or other fasteners 106 to be driven into a single vertebral body or bodies.

The bone screw 106 comprises a head portion 118 and a threaded shank 124 extending generally downwardly from the head and tapering inwardly. The head portion 118 includes an instrument recess 126 for receiving a tip of a surgical tool such as an impact driver, drill, screwdriver or the like. Various bone screws or rods 106 may be employed including ones capable of variable angle or fixed angled orientation with respect to the plate 102 with or without the ability to be locked down at a desired angle or orientation with respect to the plate 102.

The plate 102 also includes larger openings 122, and in the present embodiment, two openings, located between each pair of through holes 116 that effectively reduce the overall weight of the plate 102, as well as the amount of material needed to manufacture the plate and provides a visualization pathway to monitor bone graft progress between the vertebral bodies.

The plate 102 further includes a lock component 104 located between each pair of through holes 116. The lock component 104 does not substantially protrude from the upper surface 108 of the plate 102 in order to maintain the desired low profile as shown in FIGS. 1-3 and is generally either coplanar with the upper surface 108 or recessed slightly below the upper surface. The lock component 104 comprises a main body 128 connected to a threaded post 130. The threaded post 130 extends along the longitudinal axis of the lock component 104. The threaded post 130 is configured to hold the lock component 104 in position and prevent the lock component from coming out of the plate 102. The lock component 104 rotates relative to the plate 102, and in the plane of the surface of the plate about the longitudinal axis of the threaded post 130. The lock component 104 also allows for linear movement with respect to the plate 102 when securing bone screws 106. The edges of the lock component 104 are generally rounded so as to sit on the head of the screw 106 or rod, both of which are rounded in order to provide greater holding capacity and cover more surface area of the fastener 106. The lock component head, when in a locking position extends toward a central region of the fastener 106 thereby providing coverage over the central portion and flange or peripheral portion of the fastener head.

Figure 4:
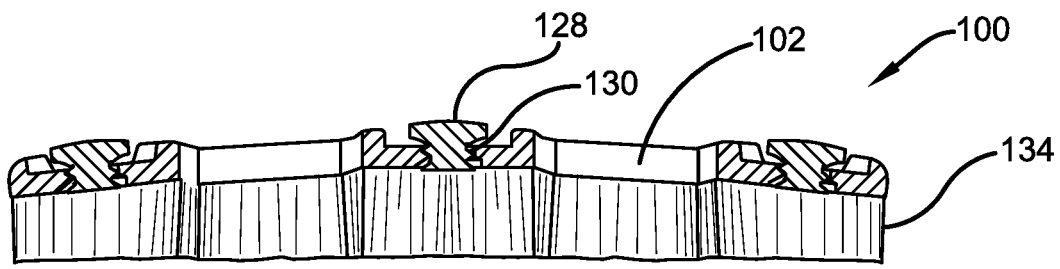
FIG. 4 illustrates a side cross-sectional view of one potential embodiment of the anterior cervical plate system having integrated locks of the present invention in accordance with the disclosed architecture.
Figure 5:
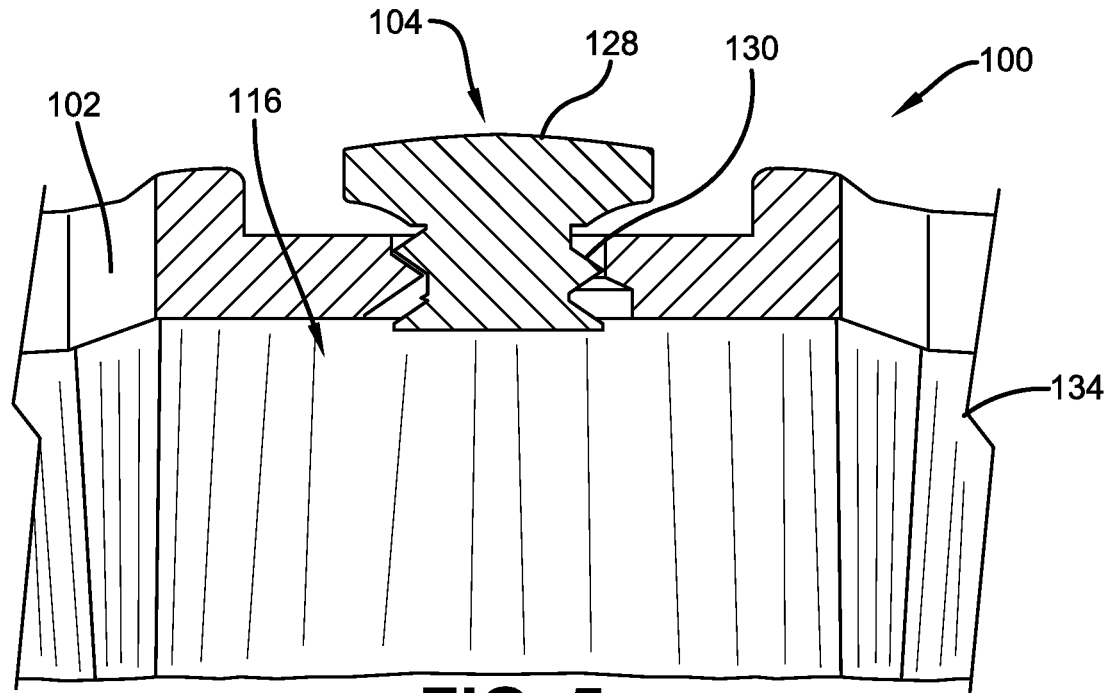
FIG. 5 illustrates a front cross-sectional view of one potential embodiment of the anterior cervical plate system having integrated locks of the present invention in accordance with the disclosed architecture.
Figure 6:
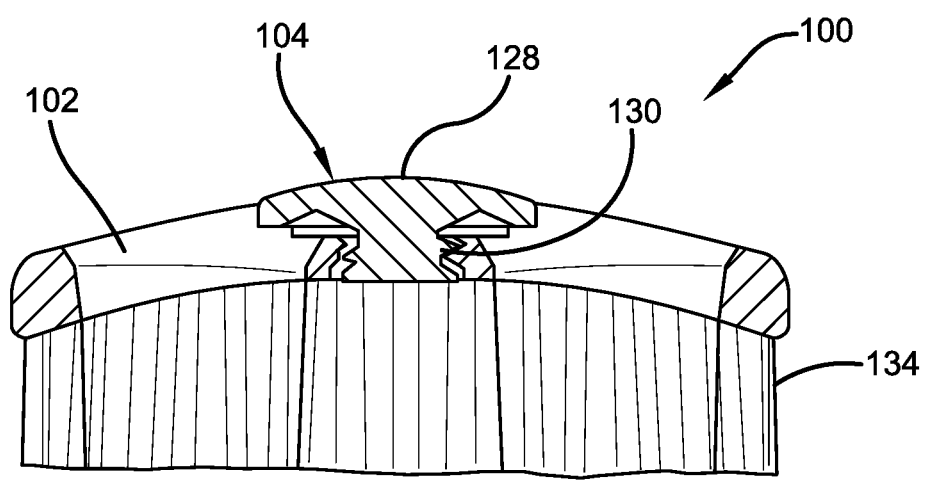
FIG. 6 illustrates a front cross-sectional view of one potential embodiment of the anterior cervical plate system having integrated locks of the present invention in accordance with the disclosed architecture.

The lock component 104 is shown in cross section in FIGS. 4-6 and is configured to receive an instrument such as a spanner wrench or other tool having a complementary shaped tip for engaging and rotating the lock component 104 between an unlocked position and a locked position or between first and second positions. The lock component 104 is positioned between two through holes 116 and configured to lock two bone screws or fasteners such as rods 106 in place and prevent back-out of the fasteners. The lock component 104 rotates approximately 90 degrees from an unlocked configuration to a locked configuration to affect a blocked and seated condition of the bone screws 106. Specifically, the main body 128 of the lock component 104 comprises a pair of locking ends 132 which when the lock component 104 is turned in a locked configuration, the pair of locking ends 132 are in a position above the through holes 116 to substantially cover the head portion 118 of the bone screws 106. The screw heads 118 of adjacent bone screws or fasteners 106 are covered simultaneously by one lock component 104. When any portion of the locking ends 132 covers the screw head 118 at least partially, back-out protection is achieved and a locked condition is affected.

Furthermore, the lock component 104 is threaded such that rotation of the lock component 104 from an unlocked configuration to a locked condition will result in the lock component 104 being threadingly drawn downwardly into the plate 102 and over the fastener head which advantageously helps the lock component 104 to be positioned closer to the bone screw 106 residing in the through hole 116. This upward and downward movement of the lock component 104 assists in unlocking and locking the bone screw 106. The lock component 104 is not only moved laterally with respect to the plate 102 but also along the vertical direction as well. The lock component 104 is configured such that the rotation of one lock component 104 will simultaneously affect a locking condition or an unlocked configuration of two bone screws 106 that are oppositely disposed with respect to the lock component 104. This two-position movement in both the horizontal plane and vertical plane secures the fastener to the bone of the individual. Of course, the system may be configured such that one lock component 104 only locks or unlocks one bone screw 14.

The lock component 104 is cylindrical in shape having a main body 128 and a threaded post 130. The threaded post 130 of the lock component 104 is sized and configured to be larger than the threaded through holes 116 formed in the plate 102. In particular, the threaded post 130 has a larger diameter portion 105 at the lower surface 110 (see e.g., FIG. 3B) of the plate 102 compared with a smaller diameter 103 portion at the upper surface 108 of the plate 102 as can be seen in FIGS. 3B, 4-6. As such, the lower larger diameter portion of the threaded post 130 is sized and configured to engage the threaded through holes 116 to prevent the lock component 104 from being removed from the plate 102. Specifically, the lock component 104 is supported in a position suspended around the plate 102 but not directly welded to the plate 102. The lock component 104 is supported in this suspended location by supports 134 that are affixed either to the plate 102 or to the build plate (not shown). The build plate is positioned below all of the supports 134 (FIG. 4) and it is typically bolted directly to the additive manufacturing machine (not shown). Once the plate 102 is additively manufactured, it is removed from the build plate, and then the supports 134 are removed from the plate 102.

In use, the anterior cervical plate 102 according to the present invention is placed or attached adjacent to a vertebral column. The placement of the plate 102 relative to the vertebral bone in a patient may be pre-operatively determined based on a pre-operative examination of the patient's spine using non-invasive imaging techniques known in the art. Next, bone screws or other fasteners 106 are inserted into through holes 116 of the plate 102 while the lock component 104 is in an unlocked position. Once the bone screws 106 are correctly positioned in the through holes 116, the lock component 104 is rotated from the unlocked configuration towards the locked configuration. To rotate the lock component 104, an instrument is inserted into the main body 128 of the lock component 104 and the lock component 104 is rotated from an unlocked position. As the lock 16 is rotated, the locking ends 132 of the main body 128 move in a position above the through holes 116 to cover the screw heads 118 of the inserted bone screws 106. The screw heads 118 of adjacent bone screws 106 are covered simultaneously by one lock component 104.

When any portion of the locking ends 132 covers the screw head 118 at least partially, back-out protection is achieved and a locked condition is affected. The surgeon may choose to continue with the rotation of the lock component 104 such that a greater portion of the screw head 118 is covered by the lock component 104. However, this is not necessary and sometimes anatomically not possible because positioning of the bone screw 106 may result in the bone screw 106 being angled with respect to the upper surface of the plate 102 such that a portion of the screw head 118 projects above the plate 102 making it impossible for the lock component 104 to further cover or completely cover the screw head 118. Advantageously, once the screw head 118 is covered by even a little of the locking end 132 further covering of the screw head 118 or completely covering the screw head 118 with further rotation of the lock component 104 to even a 90 degree orientation of the lock component 104 is not necessary with the present invention and rotation of the lock component 104 may be terminated. It is up to the surgeon's discretion to determine if the lock component 104 is adequately positioned to prevent the backing out of the bone screws 106. The locked configuration prevents the bone screw 106 from loosening and migrating back out of the through hole 116.

To remove the bone plate 102 from a patient, the same instrument is used to rotate the lock component 104 from the locked position to the unlocked configuration in which the locking ends 132 are not adjacent or covering the bone screws 106. Then an instrument can be inserted to remove the bone screws 106. The instrument is used to back out the bone screws 106.

The anterior cervical plate system 100 of the present invention provides several advantages over previous designs. For example, the lock changes height with rotation of the lock. When the locking component is moving into a locked configuration it advantageously simultaneously decreases in height. This decrease in height allows the locking ends of the lock to move closer to the screw head and even contact and press upon the screw with an additional, variable, adjustable force. For example, the amount of force applied on the patient is conveniently adjustable by the surgeon based on the surgeon's discretion with respect to the anatomy and the patient's condition. Furthermore, as the lock moves down it may contact the screw head in a locked condition. As a result, the screw or rod is prevented from toggling in a space between the screw head and the lock which may result in the future loosening of the screw or rod relative to the bone. Likewise, when unlocking the device, in the present invention, the screw head moves upwardly to create a clearance for the removal or easy adjustment of the bone screw. In the present invention, even an angled screw head can be blocked partially by a less-than-90-degree rotation of the lock. Also, the main body of the lock of the present invention is advantageously tapered downwardly such that there is less volume of the main body to interfere with a bone screw thereby being able to more easily move into a locked condition. That is, the wider portion of the locking body component is adjacent the area of the narrower portion of the screw, and the narrower portion of the locking body component is adjacent the wider portion of the screw head.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A surgical plate system comprising:
a plate having a top surface, a lower surface, and at least one opening to accommodate a fastener, the at least one opening larger at the lower surface than at the top surface; and
at least one lock component repositionable between a locked configuration and an unlocked configuration, wherein the at least one lock component is positioned adjacent to the at least one opening; and
wherein the plate and the at least one lock component are additively manufactured as a single unitary component and the at least one lock component is additively manufactured in a position that is not directly welded to the plate and is partially supported by a plurality of removable supports that are initially affixed to a build plate and removed once the plate and the at least one locking component are completed.

2. The surgical plate system of claim 1, wherein the plate comprises a textured surface for boney on-growth covering at least a portion of the lower surface of the plate.

3. The surgical plate system of claim 1, wherein the at least one lock component rotates approximately 90 degrees from the unlocked configuration to the locked configuration to affect a blocked condition of the fastener.

4. The surgical plate system of claim 3, wherein the at least one lock component comprises a pair of locking ends, and further wherein, when the at least one lock component is in the locked configuration, the pair of locking ends engage a head of the fastener.

5. The surgical plate system of claim 4, wherein the at least one lock component is threaded such that rotation of the at least one lock component from the unlocked configuration to the locked configuration will result in the at least one lock component being threadingly drawn downwardly into the plate and at least partially over the head of the fastener.

6. The surgical plate system of claim 1, wherein the at least one lock component has a body portion having a width that narrows from the top surface of the plate to the lower surface of the plate.

7. The surgical plate system of claim 2, wherein the textured surface is one of a continuous pattern, a regular pattern, or an irregular pattern.

8. The surgical plate system of claim 2, wherein the textured surface includes a plurality of shapes provided in one of a regular pattern or an irregular pattern.

9. The surgical plate system of claim 2, wherein the textured surface is comprised of a patterned portion and an unpatterned portion.

10. The surgical plate system of claim 4, wherein the pair of locking ends of the at least one locking component are rounded.

11. A cervical spine plate system comprising;
a plate having a top surface, a lower surface, a plurality of through holes and at least one visualization pathway, wherein the at least one visualization pathway is larger than at least one of the plurality of through holes;
each of the plurality of through holes is sized and configured to receive a fastener, and wherein each of the plurality of through holes comprises an exit opening in the lower surface that is larger than an entry opening in the top surface to permit insertion of the fastener at an adjustable angle of between 0° and 15°;
the lower surface of the plate having a pattern creating a topography covering at least a portion of the lower surface; and at least one locking component having a locking end and a body portion, wherein the at least one locking component is repositionable in both a horizontal plane and a vertical plane; and wherein the plate and the at least one lock component are additively manufactured as a single unitary component and the at least one lock component is additively manufactured in a position that is not directly welded to the plate and is partially supported by a plurality of removable supports that are initially affixed to the plate and removed once the plate and the at least one locking component are completed.

12. The cervical plate system of claim 11, wherein the at least one locking component is positioned adjacent at least one of the plurality of through holes.

13. The cervical plate system of claim 11, wherein the at least one locking component includes a pair of rounded locking ends to cover a head of the fastener inserted into one of the plurality of through holes to hold the fastener in the at least one of the plurality of through holes.

14. The cervical plate system of claim 11, wherein the at least one locking component is configured with a positive inclination angle of 30 degrees or less.

15. The cervical plate system of claim 11, wherein the body portion of the at least one locking component tapers downwardly and outwardly from the top surface of the plate to the lower surface of the plate.

16. A surgical plate system for use in a cervical procedure, the surgical plate system comprising:

a plate having a top surface, a lower surface, a plurality of through holes each designed to receive a bone screw, and a plurality of visual pathways each extending through the plate from the top surface to the lower surface, wherein the lower surface comprises a roughened topography portion for boney on-growth covering a portion of the lower surface and a non-textured portion covering a portion of the lower surface configured to not interfere with bony on-growth on the roughened topography portion;

a plurality of locking components, with at least one of the plurality of locking component provided adjacent at least one of the plurality of through holes and wherein each of the plurality of locking components are equally spaced apart from one another; and each of the plurality of locking components is comprised of a locking end and a body portion, wherein each of the plurality of locking components is movable in a horizontal plane to a locking position from an unlocking position to cover a head of the bone screw positioned within a through hole of the plurality of through holes; and wherein each of the plurality of through holes comprises an exit opening in the lower surface of the plate that is larger than an entry opening in the top surface of the plate to permit an adjustable angle of insertion for each bone screw; and wherein the plate and the plurality of locking components are additively manufactured as a single unitary component and each of the plurality of locking components are additively manufactured in a position that is not directly welded to the plate and is partially supported by a plurality of removable supports that are initially affixed to the plate and removed once the plate and the plurality of locking components are completed.

17. The surgical plate system for use in a cervical procedure of claim 16, wherein the plate is manufactured from one of a stainless steel, a cobalt, a titanium, an alloy, a ceramic material, and a carbon fiber and has a length ranging from 12 mm to 105 mm and a thickness ranging from 0.5 mm to 10 mm.

* * * * *